(12) United States Patent
Williams et al.

(10) Patent No.: US 6,350,412 B1
(45) Date of Patent: Feb. 26, 2002

(54) MICROSAMPLE TUBE WITH REDUCED DEAD VOLUME AND BARCODE CAPABILITY

(75) Inventors: F. Diane Williams, Durham; Michael L. Bishop; Janet B. Callahan, both of Chapel Hill; Benjamin J. Chemelli, Durham, all of NC (US)

(73) Assignee: Akzo Nobel N.V., The Netherlands (NL)

( * ) Notice: Subject to any disclaimer, the term of this patent is extended or adjusted under 35 U.S.C. 154(b) by 1295 days.

(21) Appl. No.: 08/539,466

(22) Filed: Oct. 5, 1995

Related U.S. Application Data

(62) Division of application No. 08/273,072, filed on Jul. 11, 1994, now abandoned.

(51) Int. Cl.[7] .......................... G01N 21/01; G01N 35/04
(52) U.S. Cl. ............................. 422/65; 422/63; 422/67; 422/82.05; 422/99; 422/100; 422/102; 436/47; 436/165; 436/180; 436/541
(58) Field of Search ............................. 422/58, 63, 65, 422/67, 82.05, 99, 102, 104; 436/180, 541, 47, 165; 220/420, 461, 469, 737, 739

(56) References Cited

U.S. PATENT DOCUMENTS

| | | | | |
|---|---|---|---|---|
| 1,879,820 A | * | 9/1932 | Perry ................... D24/224 X |
| 2,189,587 A | * | 2/1940 | Lallement ................... 220/737 |
| 2,873,850 A | * | 2/1959 | Ortegren ................ 422/104 X |
| 3,138,280 A | * | 6/1964 | Shafer ..................... 220/739 X |
| 3,738,527 A | * | 6/1973 | Townsend ............... 220/461 X |
| 4,015,940 A | * | 4/1977 | Conlon ........................ 422/104 |
| 4,021,124 A | * | 5/1977 | Sarstedt ....................... 356/246 |
| 4,094,641 A | * | 6/1978 | Friswell ....................... 436/180 |
| 4,106,907 A | * | 8/1978 | Charlton et al. ........... 23/230.3 |
| 4,221,303 A | * | 9/1980 | Yoshimura et al. ......... 220/461 |
| 4,272,478 A | * | 6/1981 | Vihko .......................... 422/57 |
| 4,624,835 A | * | 11/1986 | Davis et al. ................. 422/102 |
| 4,628,036 A | * | 12/1986 | Scheepens et al. .......... 436/520 |
| 4,758,409 A | | 7/1988 | Uffenheimer ............... 422/102 |
| 4,832,916 A | * | 5/1989 | Gilak ........................... 422/70 |
| 4,873,633 A | * | 10/1989 | Mezei et al. ........... 364/413.08 |
| 4,878,597 A | * | 11/1989 | Haast .......................... 220/404 |
| D310,264 S | * | 8/1990 | Leoncavallo et al. ......... D24/29 |
| 4,968,486 A | * | 11/1990 | Zander ........................ 422/102 |
| 4,982,872 A | * | 1/1991 | Avery .......................... 220/461 |
| 4,997,691 A | * | 3/1991 | Parkinson .................. 428/35.7 |
| D318,727 S | * | 7/1991 | Spike ........................ D24/224 |
| 5,030,421 A | * | 7/1991 | Muller ........................ 422/102 |
| 5,038,852 A | * | 8/1991 | Johnson et al. ............... 165/12 |
| 5,038,958 A | | 8/1991 | Dreier ........................ 220/336 |
| 5,150,812 A | * | 9/1992 | Adams ........................ 220/414 |
| 5,203,470 A | * | 4/1993 | Brown ........................ 220/462 |
| 5,236,666 A | * | 8/1993 | Hulette et al. ................ 422/65 |
| D342,028 S | * | 12/1993 | Stenger ...................... D24/224 |
| 5,310,527 A | | 5/1994 | Romanauskas et al. ..... 422/102 |
| 5,344,036 A | * | 9/1994 | Stanescu et al. ............. 215/251 |
| 5,344,045 A | * | 9/1994 | Richter et al. .................. 222/1 |
| 5,443,791 A | * | 8/1995 | Cathcart et al. .............. 422/65 |

OTHER PUBLICATIONS

Catalog, Cole—Parmer Instrument Company, 1993–1994 printed in 1992, pp. 1409–1411.*
Catalog, Cole–Parmer Instrument Company, 1993–1994, printed in 1992, pp. 1409–1410.*

* cited by examiner

Primary Examiner—Harold Pyon
(74) Attorney, Agent, or Firm—Myers Bigel Sibley & Sajovec, P.A.

(57) ABSTRACT

A micro sample tube is disclosed which is of a standard size on the exterior, but which has a reduced internal volume. A slope of an inner wall of the sample tube is a second order or higher curve, and is preferably a circle. Dead volume is reduced, and standard barcode labels can be used, due to the restricted internal dimensions and standard external dimensions. The curved inner wall of the sample tube, and an internal length of the sample tube which is the same as a conventional tube, reduces the likelihood of a sample probe of an automated analyzer impacting on an inner surface of the sample tube and potentially gouging the tube and/or damaging the automated probe. In a preferred embodiment, fins extend around said tube for reduced weight and improved heat transfer of the micro sample tube.

17 Claims, 7 Drawing Sheets

MICROSAMPLE TUBE WITH REDUCED DEAD VOLUME AND BARCODE CAPABILITY

CROSS REFERENCE TO RELATED APPLICATIONS

This is a divisional of application Ser. No. 08/273,072 filed Jul. 11, 1994, now abandoned.

This application is related to the following U.S. patent applications, the disclosures of which are incorporated herein by (1) Ser. No. 07/833,950, to Hulette et al, entitled "Temperature Regulation in a Sample Handling System for an Optical Monitoring System", now U.S. Pat. No. 5,236,666, which is a continuation-in-part of U.S. patent application Ser. No. 07/443,951, now abandoned;

(2) Ser. No. 07/443,952 to Swope et al, entitled "Multichannel, Optical Monitoring Systems", now U.S. Pat. No. 5,002,392;

(3) Ser. No. 07/443,956, to Karp et al, entitled "Sample Tube and Linear Drive Mechanism Therefor", now U.S. Pat. No. 5,040,894;

(4) Ser. No. 07/443,954, to Hoffman et al, entitled "Apparatus and Method for Cleaning Reagent Delivery Probes", now U.S. Pat. No. 4,989,623;

(5) Ser. No. 07/674,957 to Keiter et al., entitled, "Heated Liquid Sampling Probe for an Automated Sampling Apparatus", now U.S. Pat. No. 5,178,019;

(6) Ser. No. 07/916,712 to Lewis et al, entitled "Cassette and Cuvette Loading Mechanism"; and (7) Ser. No. 07/443,953, to Driscoll, titled, "Method of Monitoring Reagent Delivery in a Scanning Spectrophotometer", now U.S. Pat. No. 5,068,181.

BACKGROUND OF THE INVENTION

The present invention relates to a micro sample tube for holding a sample in an automated sampling system. More particularly, the present invention relates to a micro sample tube having a) a standard size exterior so as to allow for marking with, for example, bar codes, and so as to allow for use in an automated analyzer geared for holding and/or moving of sample tubes of a same standard size, b) a uniquely designed interior for minimizing internal dead volume, as well as for decreasing the incidence of detrimental impact of a sample probe against an interior wall of the micro sample tube, and c) an improved structure for increasing heating and/or cooling of the sample tube.

Automated sample handling systems are known which automatically dispense patient fluid samples, such as blood plasma, along with reagents and other additives, into the reaction well of a cuvette which is then automatically positioned for monitoring or performing tests on the fluid sample. For example, in U.S. application Ser. No. 07/833,950, now U.S. Pat. No. 5,236,666, to Hulette et al, entitled "Temperature Regulation in a Sample Handling System for an Optical Monitoring System", there is disclosed an automated sample handling system for an optical evaluation instrument that can handle a high throughput of patient samples with a high degree of versatility, adaptability and reliability. The invention according to Hulette et al allows for walk-away automation for a sample handling system, once sample tubes containing patient samples are loaded into the system.

Accurate positioning and stabilizing of the sample tube within an automated system is essential. For example, in the aforementioned system disclosed by Hulette et al, a sample tube is advanced to a piercer where a piercing probe can be caused to pierce the septum of the sample tube. This step would be omitted, of course, should a sample tube without a cap be used. A sample probe is lowered a predetermined distance into the sample tube to aspirate a programmed amount of sample. The sample probe is then removed from the sample tube and the sample subsequently dispensed into a cuvette. Accurate positioning of the probe into the sample tube, without gouging or puncturing the internal side wall of the sample tube, is important.

Automated analyzers have been developed which can automatically perform analyses on multiple patient samples without operator intervention, where it is possible to track specific patient samples by means of bar code labels. Sample volume containers with bar code information on the side identifying the sample and the test to be performed by the analyzer are loaded into, for example, a temperature controlled compartment, which also stores reagents and other additives under temperature control. The samples are automatically dispensed into reaction wells of cuvettes, and reagents and possibly other additives are automatically combined with the test samples according to the programmed test read from the bar code on the sample container. The reaction wells containing a reaction volume composed of a test sample and additives are transported to an optical analyzer which monitors changes in optical characteristics of the reaction volume, which changes are processed and evaluated according to the particular test being performed. Such a machine is capable of reading the bar codes on hundreds of patient samples, keeping track of such patient samples, and performing tests on such samples without intervention of the operator once the sample containers are loaded into the temperature controlled compartment. As such, the ability to have a bar code on the exterior of a sample container, regardless of the sample size, is important for the automated analysis.

Regarding the temperature control of the samples, a temperature controlled housing can be provided for storing the fluid samples and reagents at a relatively cool temperature for preventing degradation of the samples and reagents at a temperature of, for example 4 degrees C. For this reason, a micro sample tube with improved heat transfer capabilities, would be desirable.

Sample tubes are manufactured in various brands and sizes. For example, sample tubes manufactured by Beckton Dickinson of Rutherford, N.J. and sold under the brand name Vacutainer with Hemogard Closure, typically have a length of 75 mm and a diameter of 13 mm. In contrast, sample tubes made by Sarstedt and sold under the brand name of Monovette Microtainer can have a length of 65 mm and a diameter of 12 mm. Consequently, the aforementioned automated systems typically are limited to using one standard size of sample tube for all tests and procedures to be run, or by requiring that all of the sample tubes of a particular transport rack be of the same size. However, at times when very small quantities of a sample are analyzed, an undesirably large amount of sample fluid remains in a standard size sample tube and cannot be removed by the sample probe. This remaining fluid (dead volume) is therefore wasted and tests that otherwise might have been performed, are foregone.

SUMMARY OF THE INVENTION

It is therefore an object of the invention to provide a sample tube for an automated analyzer that, on the exterior, is of a standard size so as to be easily handled by the analyzer, and so as to allow for the placement of a bar code label on an exterior surface of the sample tube.

It is another object of the invention to provide a sample tube with a standard size on the exterior, but with a restricted internal volume so as to allow handling of small volume samples, but with a minimum of dead space within the sample tube.

It is a further object of the present invention to provide a sample tube of standard size exterior, and restricted size on the interior, with interior walls having a unique structure that helps avoid gouging of the walls of the restricted interior by an automated fluid sampling probe.

It is yet another object of the present invention to provide a sample tube having an exterior structure which aids in heating and/or cooling of the sample tube.

The above and other objects are accomplished according to the invention by the provision of a sample tube having an outer wall defining an exterior of the sample tube, the cross section of which is substantially circular with substantially constant cross sectional area along the length of the tube, the outer wall defining a central axis of the sample tube, an open end at one axial end of the sample tube, and a closed end at the other axial end of the sample tube, and an inner wall defining an interior of the sample tube, the inner wall having in at least a portion thereof, a slope towards the central axis of the sample tube in the direction of the closed end, the slope of the inner wall in cross section, defining a portion of a circumference of a circle. Fins may be provided extending from the inner wall and defining in part the outer wall.

The invention will be described below in greater detail in connection with an embodiment thereof that is illustrated in the drawing figures.

BRIEF DESCRIPTION OF THE DRAWINGS

The foregoing objects and advantages of the invention, together with other objects and advantages which may be attained by its use, will become more apparent upon reading the following detailed description of the invention taken in conjunction with the drawings. In the drawings, where like reference numerals identify corresponding components.

DETAILED DESCRIPTION OF THE INVENTION

Figure 1:
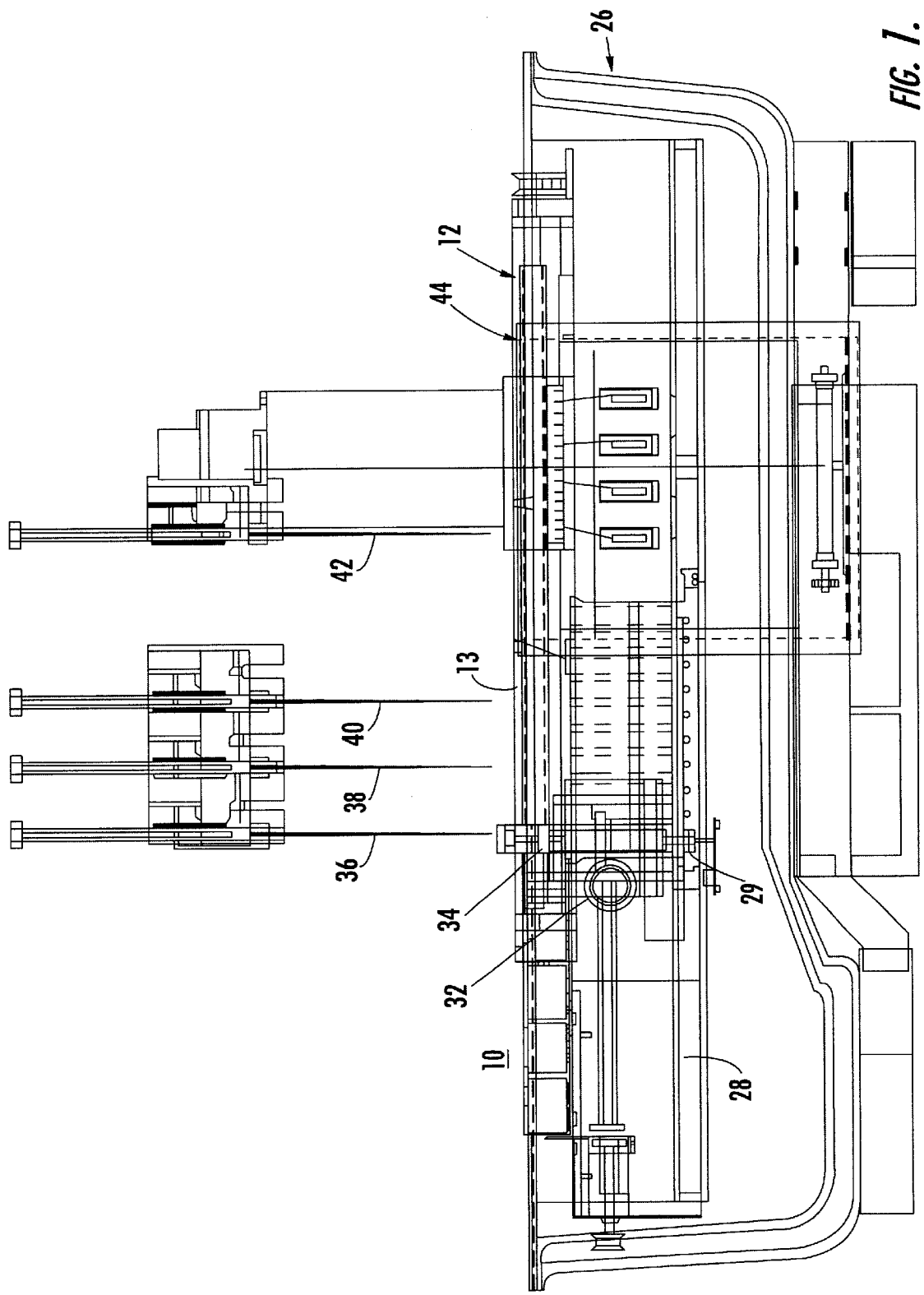
FIG. 1 is a cross sectional view of an automated analyzer in which the sample tube of the present invention can be used.

Referring to FIG. 1, there is illustrated a sample handling system including a cuvette storage and loading mechanism 10, for supplying cuvettes individually to a cuvette transport mechanism 12, which advances the cuvettes along a linear track 13. The sample handling system additionally includes a temperature controlled housing 26, for storing a plurality of sample/collection tubes, which are transported via shuttles 28 through a programming station having a bar code reader 32, for reading a preprinted bar code printed on the side of each sample tube identifying the test sample and the test to be performed, and onto sample insertion station which includes a piercer 34, for piercing the septum of a collection tube for allowing a sample probe 36 to be lowered into the sample collection tube for aspirating a fluid sample which is to be ejected into a reaction well of a cuvette located at a sample insertion station. Temperature controlled housing 26, additionally encloses a reagent chamber which stores a plurality of reagent containers, which can be accessed by reagent probes 38, 40 and 42 for aspirating selective reagents and injecting them into reaction wells located at respective reagent insertion stations. As used herein, reagents include any reagent, diluent, buffer, or activator which is required for any given biochemical test being performed on the patient sample according to a preprogrammed test protocol. A probe washing station 44, is provided for washing the sample and reagent probes after each dispensing action.

Each shuttle 28 is provided with means for carrying a plurality of sample tubes. A drive mechanism comprising gears which mesh with gear tracks 29 on the bottom of the shuttles 28 drive the shuttles. The shuttles are transported, one behind the other, so that the collection tubes are passed first through programming station 30 where bar code reader 32 reads a previously-applied bar code on the side of the sample tube to identify the sample and the test to be performed. The information read by the bar code reader 32 is fed to the instrument controller for controlling subsequent movement of the sample and reagent probes for filling a reaction well of a cuvette transported by cuvette transporting mechanism 12 through the respective sample and reagent stations.

Figure 2:
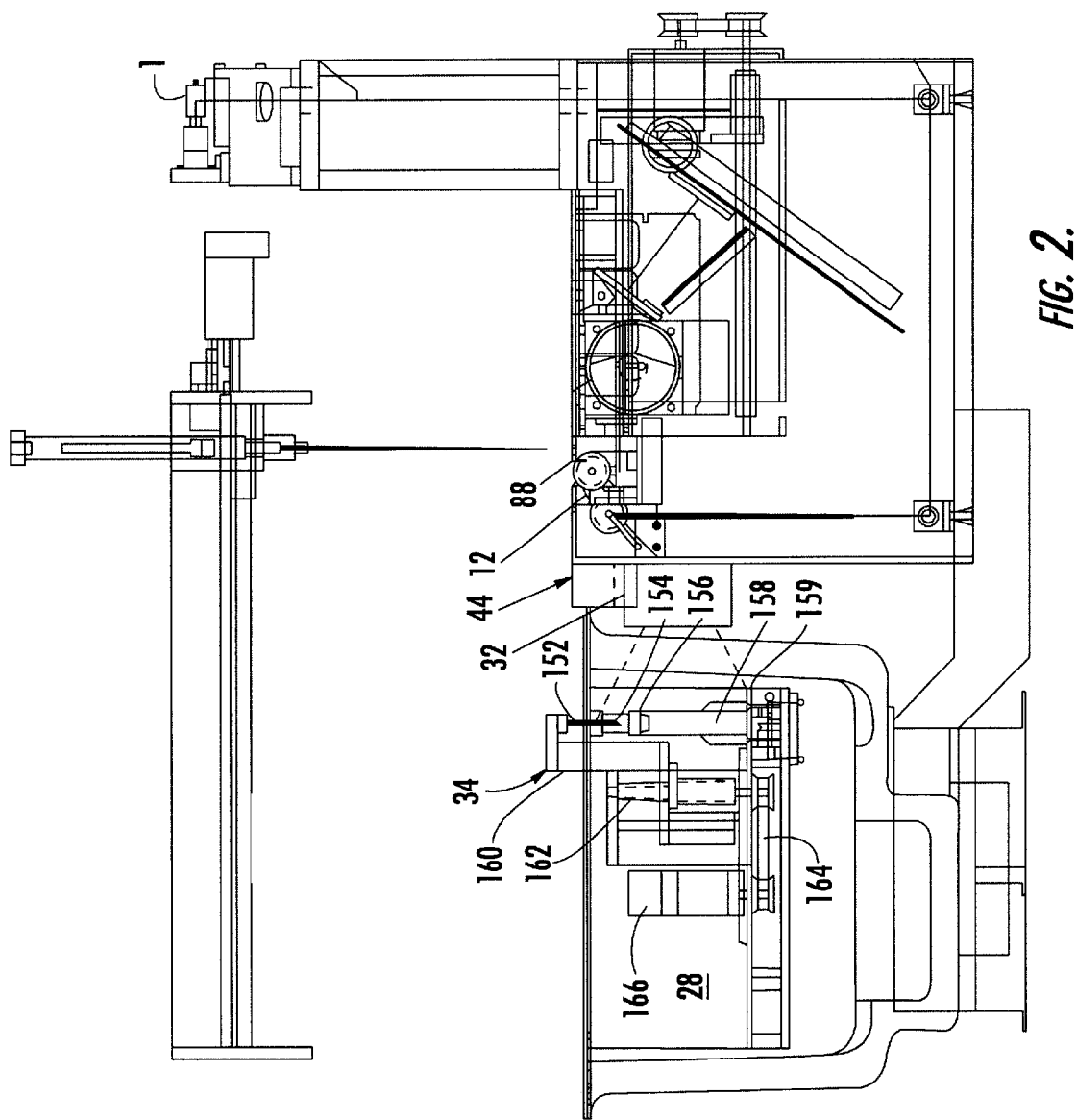
FIG. 2 is another cross sectional view showing further features of the automated analyzer in which the sample tube of the present invention can be used.

After having its bar code read, the sample tube is moved, by way of the shuttle and shuttle drive mechanism, a precise distance to place the collection tube in line with piercer 34. As can be seen in FIG. 2, piercer 34 includes a piercing tube 152 having a sharp angled end 154, canted at approximately the same angle as the tip of a conventional hypodermic needle, for piercing a septum 156 of an evacuated collection tube 158. Piercing tube 152 is mounted in a support 160 which engages a vertical lead screw 162 which is connected by way of a belt and pulley system 164 to a motor 166 for driving lead screw 162. With appropriate movement of lead screw 162, piercing tube 152 is cause to be lowered for piercing septum 156 or to be removed therefrom. A holding mechanism 159 holds tube 158 in place while piercing tube 152 is inserted and withdrawn. Piercer 34 has an opening at the top concentrically aligned with piercing tube 152, so that when sample probe 36 is aligned with piercing tube 152, a pathway is provided for lowering the sample probe into a sample tube 158, for aspirating a fluid sample therefrom.

Figure 3:
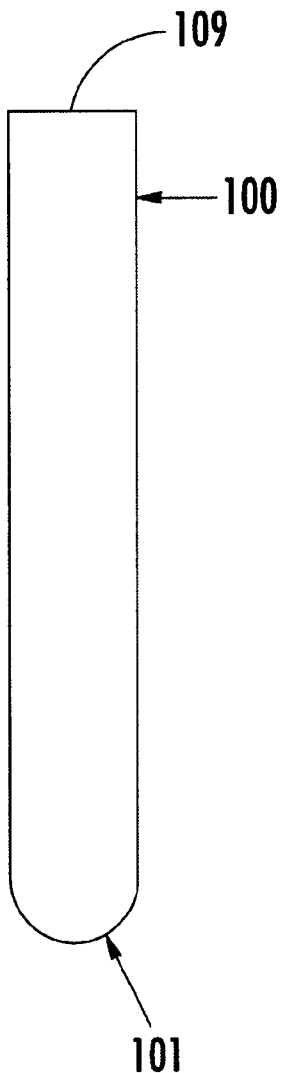
FIG. 3 is a cross sectional view of a conventional freezer tube.

The above-mentioned automated analyzer is, of course, but one example of an analyzer contemplated for use with the sample tube of the present invention. Due to the automated nature of the sample handling system as set forth above, or of other automated analyzers, it is desirable for the sample tubes carried by shuttles 28 to have standard dimensions. For example, a standard exterior of the sample tube is desirable for ease in the automated handling. A common conventional sample tube is a 12 mm (diameter)×75 mm (length) freezer tube. The present invention is contemplated as being of particular use in an automated analyzer that is geared for handling such 12×75 tubes, though a range of dimensions is possible. As can be seen in FIG. 3, a conventional sample tube 100 of standard type having a standard curved bottom portion 101 and open end 109 is easily handled by the automated handing system. Shuttles 28 are designed to be compatible for holding the exterior of the standard size tube, and probe 36 is geared for movement a standard distance to the bottom 101 of the sample tube 100.

Problems arise however, when small quantities of a sample are desired to be handled by the automated handling system. For example, large volume samples sometimes can not be obtained in pediatric and animal testing. Though a smaller sample tube could be manufactured, the use of such a small tube results in problems with handling such a tube in an automated analyzer geared to handle a larger standard size tube. In addition, standard caps can not be used on such a smaller tube, and bar code labels can not be fit and/or read properly on a smaller tube. Furthermore, a lesser depth of a smaller tube requires more cumbersome handling of the tube. For example, it might be necessary to alter the depth alignment of the sample probe of the automated analyzer in order to avoid the sample probe impacting the bottom surface of the sample tube. This alteration of the movement parameters of the automated analyzer is inefficient and inconvenient.

Figure 4:
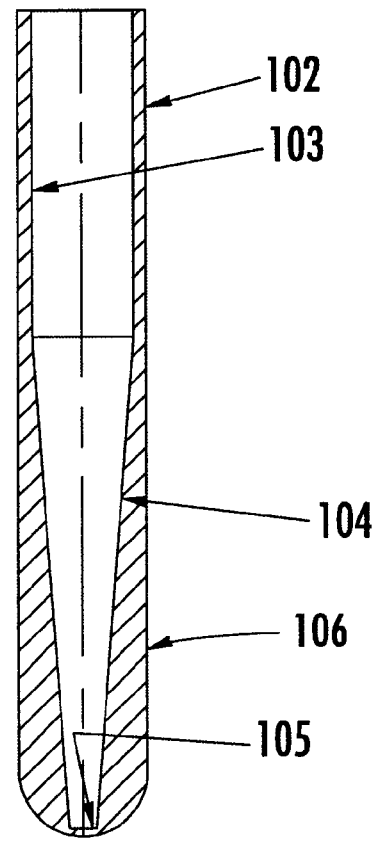
FIG. 4 is a cross sectional view of one embodiment of the sample tube of the present invention.

In accordance with the present invention, as can be seen in FIG. 4, a sample tube is provided which can minimize dead volume within the tube when small volume samples are disposed therein, while at the same time, the overall circumference and internal depth of the tube remain the same so that such a tube can be used in an automated analyzer set up for a larger sample tube. Sample tube 104 has an upper internal wall portion 103 of substantially constant diameter. However, as can be seen beginning approximately at the lower half of the sample tube 102, a lower internal wall portion 104 slopes constantly and gradually inwardly thus reducing the internal volume in this portion of the sample tube. The wall portion 104 curves at a constant rate from the midpoint of the tube to the bottom of the tube. However, the internal wall portion 104 can extend all the way towards the top of the sample tube, though preferably not so high as to interfere with the ability to use a standard cap on the sample tube.

The dead volume of sample tube 102 is less than 50 microliters for an automated analyzer such as disclosed in the aforementioned Hulette et al. patent. The maximum depth at portion 105 of sample tube 102, as well as the overall outer circumference of the sample tube, are the same as for a standard sample tube 100 as shown in FIG. 3. For example, if an automated analyzer is set up for handling standard 12×75 freezer tubes, sample tube 102 can be designed to have the same outer circumference as well as the same length and internal depth, as a standard 12×75 tube. As such, the two tubes can be used interchangeably in the same automated analyzer.

Figure 5A:
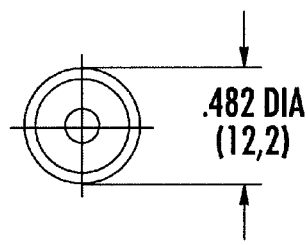
FIGS. 5a, 5b and 5c are views of the sample tube of the present invention with preferred dimensions of the tube.
Figure 5B:
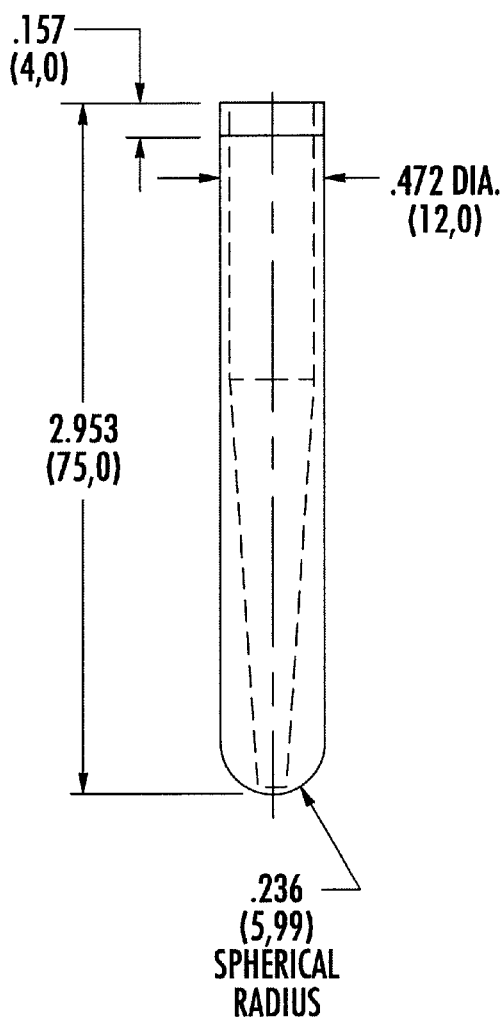
Figure 5C:
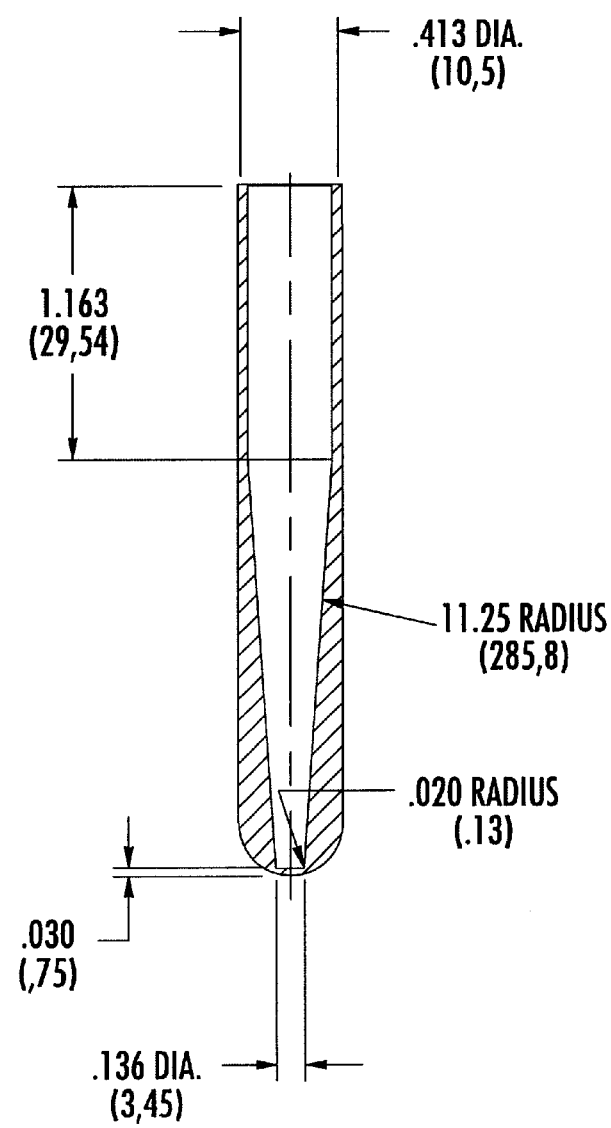

Preferred dimensions (in inches, with dimensions in millimeters in brackets below) of the sample tube are shown in FIGS. 5(a) to 5(c). Lower internal wall portion 104 (FIG. 4) has a preferred radius of curvature of 11.25 inches (285.75 mm). In other words, if the convex curve of internal wall 104 were to be extended to form a circle, the radius thereof would be 11.25inches. This curving nature of the internal wall of the sample tube has been found to be very helpful in avoiding gouging of the internal wall by the sampling probe when descending down into the sample tube. Though a straight V-shaped internal wall structure can reduce internal dead volume, a convex curved internal wall provides a taper for guiding the probe to the bottom of the tube in contrast to a V-shaped structure which can cause the probe to dig into the side wall and potentially damage the probe. This feature of the inner wall is also explained hereinbelow in connection with FIG. 8.

Figure 6A:
FIGS. 6a and 6b are side and bottom views, respectively, of another embodiment of the present invention where the sample tube has fins.
Figure 6B:
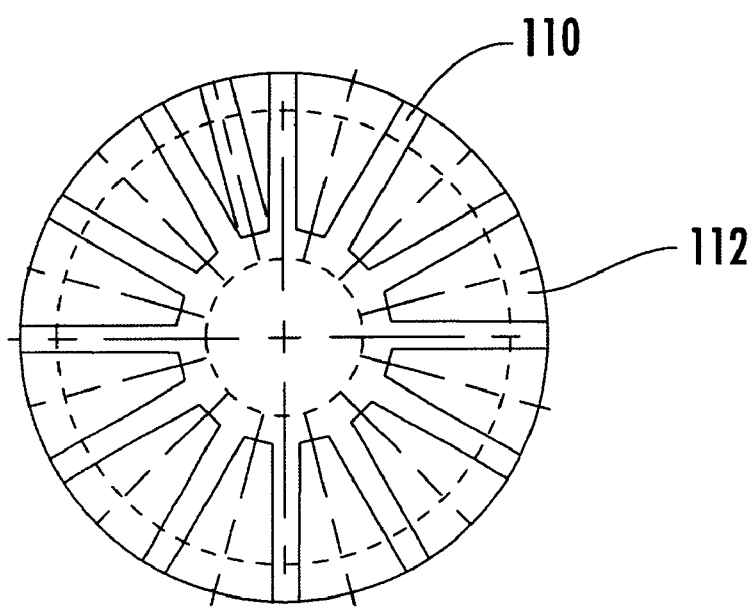

As can be seen in FIG. 4, the make-up of the sample tube between the outer wall of the tube and the inner sloping wall, is a solid mass of the material from which the sample tube is made, such as polypropylene plastic. However, in another preferred embodiment such as illustrated in FIGS. 6a and b, rather than a solid mass of polypropylene, the sample tube structure may comprise alternating fins 110 and grooves 112. This arrangement is helpful for reducing the mass of the sample tube, and can aid in heat transfer should heating or cooling of the sample tube be necessary. As illustrated in FIG. 6b, 12 fins can be disposed at 30 degree intervals, but, of course, a greater or fewer number of fins can be used. In addition, rather than longitudinal fins such as illustrated in FIGS. 6a and b, the fins can extend laterally (circumferentially) around the sample tube, with the depth of the fins (and alternating grooves) decreasing towards the open end of the sample tube. Also, a combination of both longitudinal and lateral fins could be used. Or, one or more helical fins could be formed in the sample tube. Other fin arrangements are also possible.

Figure 7:
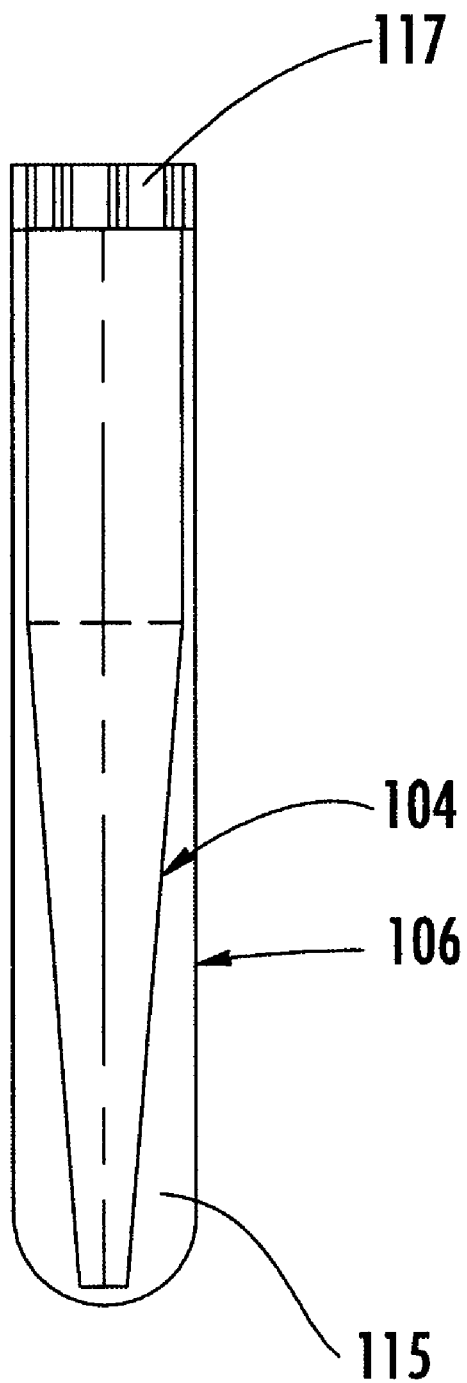
FIG. 7 is a cross sectional view of another embodiment of the sample tube of the present invention.

In a still further embodiment, as illustrated in FIG. 7, the sample tube could include a hollow area 115 filled with air between the inner tapered wall 104 and the exterior wall 106. Or, this inner area 115 could be filled with a material different from the material used for forming the inner and outer walls. The inner area 115 could be filled, for example, with an insulating substance, a conducting material, a foamed lightweight material, etc., depending on the desired end characteristics of the sample tube. Of course, in any case, the semi-circular curving nature of the internal wall 104 should remain.

As also illustrated in FIG. 7, a barcode label 117 can be attached to the exterior of the sample tube. Barcode labels are often available in standard sizes from manufacturers. As such, it may be difficult or impossible to obtain a barcode label for a sample tube varying from the standard industry dimensions. In addition, even if the standard barcode label were to be attached to, for example, a tube much smaller than a standard size tube, there still could result a difficulty in reading the barcode by the barcode reader of the automated analyzer. For this reason as well, it is important for the exterior dimensions of the sample tube of the present invention, to be the same as the conventional sample tubes.

In experiments conducted by the inventors, a sample tube having only a V-shape sloping internal wall was used, with 500 microliters of water. The sample tube was placed in an automated analyzer and testing was performed to see how many times 50 microliters of water could be picked up before there was a liquid level sense error. The probe sampled 7 times from the V-shaped tube before a liquid level sense error was detected, which showed that 350 microliters was sampled, thus leaving a dead space volume of 150 microliters. The process was repeated without any additional water added to the tube. The sample probe sampled 2 more times before a liquid level sense error was detected, which meant that 100 microliters was taken from the tube, leaving a dead space volume of 50 microliters. On the third pick-up of the sample probe, however, the probe hit the side of the V-shaped inner wall of the sample tube, which gouged the inner wall and caused a leak in the tube. Therefore, the V-shaped tube was determined to be inconsistent and inadequate in comparison to the unique structure of the sample tube of the present invention.

Three prototypes of the present invention were constructed, each having a 12-fin arrangement, such as illustrated in FIGS. 6a and b. The tubes were first cleaned with DI water than ethanol and were dried completely with an applicator stick. A measured amount of plasma was put into each tube and tests were ordered for the barcoded tubes. After the tests were completed, the dead volume was measured for each tube. The testing was repeated multiple times using varying amounts of plasma. After completion of the testing it was determined that the dead volume averaged less than 40 microliters (and each within a range of 30 to 45 microliters. Both lipemic and hemolyzed samples were tested, without any incidences of gouging of the curved inner sidewalls.

Figure 8:
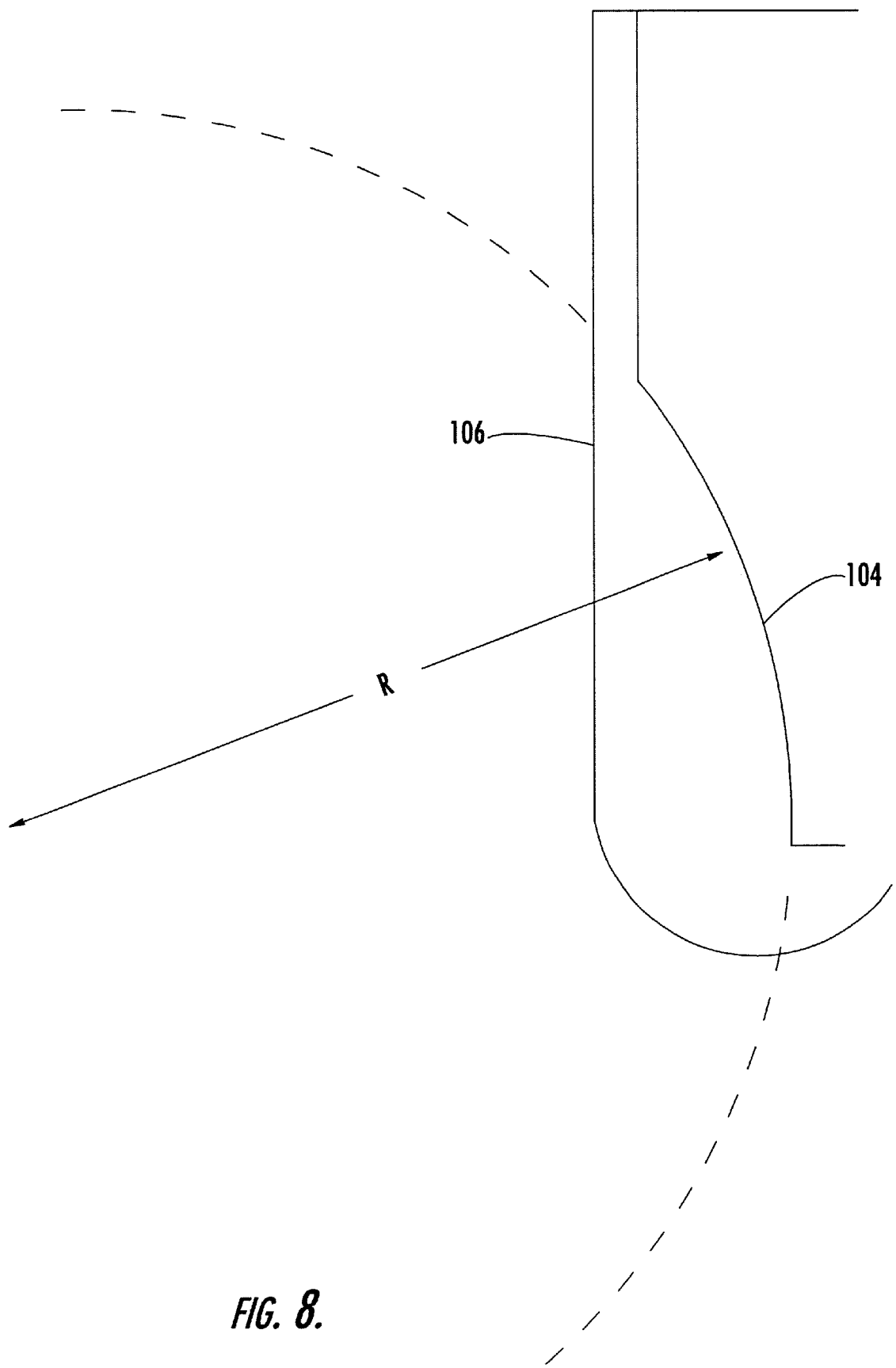
FIG. 8 is a diagram illustrating the curved nature of the inner wall of the sample tube of the present invention.

From the tests conducted, a curved inner sidewall surface that, in cross section, defines a portion of a circumference of a circle, was found to be effective in avoiding gouging of the inner wall. As can be seen in FIG. 8, the outer wall 106 of the sample tube extends vertically, whereas at least a portion of the inner wall 104 has a surface which defines in part, the circumference of a circle of radius R. In particular, a radius of from 6 to 16 inches, preferably from 9 to 13 inches, and more preferably approximately 11 ¼ inches, was found to provide an inner surface effective in preventing gouging by a sample probe. Though a curve defining a circumference of a circle was found to be particularly effective in guiding the probe to the bottom of the sample tube without gouging, the curve need not necessarily be semi-circular.

Other second order curves or higher order curves are also contemplated.

Additional testing of the sample tube of the present invention showed that it is freezable at −70 degrees C. for extended periods of time, and that the sample tube has the same or enhanced liquid sense properties as a conventional 12×75 freezer tube. Testing of liquid sense circuitry was performed using an automated analyzer and an oscilloscope, which showed that the sample tube of the present invention had the same or better response than the conventional freezer tube.

The sample tube of the present invention can be manufactured in a number of ways. In particular, injection molding of the tube is contemplated, though machining by hand or otherwise, or other molding methods could also be used. A wide variety of polymers, including polypropylene, can be used to make the sample tube of the present invention.

The sample tube as described herein, therefore, results in the benefit that the exterior of the tube can conform to the exterior dimensions of standard sample tubes and thus is of sufficient size for placement of a barcode label thereon. However, the sample tube of the present invention has a restricted interior, which helps in reducing internal dead space. The unique sloping of the internal wall of the sample tube of the present invention helps reduce gouging of sample tube so as to avoid potential leakage of the tube and/or damage to a probe in an automated analyzer. Fins disposed on the sample tube allow for a lighter weight tube, less waste of manufacturing materials, and improved heat transfer.

The invention has been described in detail with particular reference to preferred embodiments thereof, but it will be understood that variations and modifications can be effected within the spirit and scope of the invention as described herein above, and as defined in the appended claims.

What is claimed is:

1. A method of sampling micro-volumes of fluid from a micro-sample tube comprising:

positioning a polymeric micro-sample tube in a position for sampling within an automated analyzer, said micro-sample tube having an outer wall defining a central axis of the micro-sample tube, a first end having an opening at one axial end of the micro-sample tube, and a closed end at the other axial end of the micro-sample tube, and an inner wall made of a polymer material defining an interior of the micro-sample tube, the inner wall having in at least a portion thereof, a slope towards the central axis of the micro-sample tube in the direction of the closed end, the slope of the inner wall in cross-section, defining a convex curve in relation to the interior of the tube;

automatically moving an automated probe to a position above the micro-sample tube;

automatically lowering the automated probe a distance into the micro-sample tube, wherein said polymer inner wall of said micro-sample tube having a convex curve in cross-section deflects said automated probe so as to avoid gouging of the inner wall of the micro-sample tube by the automated probe should the automated probe impact the inner wall of the micro-sample tube;

aspirating a volume of fluid sample from the micro-sample tube; and moving the automated probe from the micro-sample tube and subsequently dispensing the fluid sample from the automated probe.

2. A method of sampling micro-volumes of fluid according to claim 1, wherein the convex curve of the inner wall of said micro-sample tube in said automated analyzer is a second or higher order curve, and wherein when said automated probe impacts said second or higher order curved inner wall, said inner wall deflects said automated probe.

3. A method of sampling micro-volumes of fluid according to claim 2, wherein said second or higher order curve is a circle defined by the equation $r^2 = x^2 + y^2$ where r is the radius of the circle with its center at the origin (0,0) in a Cartesian coordinate system.

4. A method of sampling micro-samples of fluid according to claim 1, wherein the diameter of the micro-sample tube is from 10 to 15 mm and the length is from 50 to 100 mm.

5. A method of sampling micro-volumes of fluid according to claim 4, wherein the diameter of the microsample tube is 12 mm and the length is 75 mm.

6. A method of sampling micro-volumes of fluid according to claim 1, wherein in said fluid sample dispensing step, the fluid sample is dispensed from the automated probe into a reaction well of a cuvette located at a sample insertion station.

7. A method of sampling micro-volumes of fluid according to claim 6, further comprising adding at least one reagent into said reaction well of said cuvette to obtain a reaction between said at least one reagent and said fluid sample.

8. A method of sampling micro-volumes of fluid according to claim 1, wherein a plurality of sample tubes are consecutively positioned for sampling within an automated analyzer, at least one of said plurality of sample tubes is said micro-sample tube, each of said plurality of sample tubes having uniform exterior dimensions and at least said micro-sample tube having a decreased internal volume due to said convex curving inner wall.

9. A method of sampling micro-volumes of fluid according to claim 8, wherein each of said plurality of sample tubes including said micro-sample tube which has the same upper dimensions and each comprises a cap of the same size.

10. A method of sampling micro-volumes of fluid according to claim 9, wherein each of said plurality of sample tubes including said micro-sample tube which has a respective bar code label on an exterior thereof.

11. A method of sampling micro-volumes of fluid according to claim 10, further comprising:
   reading the bar code label on each of said plurality of sample tubes including said micro-sample tube;
   taking a sample from each of said plurality of sample tubes by piercing the cap of each sample tube with said automated probe; and
   performing at least one test for each sample tube based on information retrieved due to reading the respective bar code label.

12. A method of sampling micro-volumes of fluid according to claim 8, wherein each of said plurality of sample tubes including said micro-sample tube has a same internal depth.

13. A method of sampling micro-volumes of fluid according to claim 1, wherein said micro-sample tube comprises a plurality of fins, and wherein in said positioning step, said micro-sample tube is in the position for sampling within the automated analyzer, said position including cooling such that the sample in said micro-sample tube is cooled, and wherein said plurality of fins aid in heat transfer so as to improve said cooling.

14. A method of sampling micro-volumes of fluid according to claim 1, wherein said micro-sample tube comprises a conducting material between an outer wall of said micro-sample tube and said convex curved inner wall, and wherein in said positioning step, said micro-sample tube is in the position for sampling within the automated analyzer, said position including cooling such that the sample in said micro-sample tube is cooled, and wherein said conducting material aids in heat transfer so as to improve said cooling.

15. A method of sampling micro-volumes of fluid according to claim 3, wherein a radius of curvature of said inner wall is from 6 to 16 inches.

16. A method of sampling micro-volumes of fluid according to claim 15, wherein the radius of curvature of said inner wall is from 9 to 13 inches.

17. A method of sampling micro-volumes of fluid according to claim 15, wherein said micro-sample tube is an injection molded sample tube.

* * * * *